(12) United States Patent
Wise et al.

(10) Patent No.: US 7,997,300 B1
(45) Date of Patent: Aug. 16, 2011

(54) AEROSOL INLET FLOW MODULATOR

(75) Inventors: Daniel G. Wise, Ellicott City, MD (US);
Lawrence J. Hyttinen, Abingdon, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 291 days.

(21) Appl. No.: 11/417,305

(22) Filed: Apr. 11, 2006

(51) Int. Cl.
*B01F 5/00* (2006.01)
*G01N 1/38* (2006.01)
*G01N 30/38* (2006.01)

(52) U.S. Cl. .............. 137/601.18; 73/23.41; 73/23.42; 73/863; 366/336

(58) Field of Classification Search ........... 137/599.01, 137/601.18, 601.19, 219, 222; 366/338, 366/336, 341; 73/23.41, 863, 23.33, 23.42; 138/40; 181/227; 60/276
See application file for complete search history.

(56) References Cited

U.S. PATENT DOCUMENTS

| 1,700,111 | A | * | 1/1929 | Welcker | 137/220 |
|---|---|---|---|---|---|
| 2,825,203 | A | * | 3/1958 | Bertin et al. | 60/249 |
| 2,912,821 | A | * | 11/1959 | Horak | 60/249 |
| 2,924,237 | A | * | 2/1960 | Ellis | 137/599.18 |
| 4,003,401 | A | * | 1/1977 | Haring | 137/599.18 |
| 4,438,049 | A | * | 3/1984 | Ammons | 137/601.18 |
| 6,220,272 | B1 | * | 4/2001 | Tavor | 137/219 |
| 6,786,075 | B2 | * | 9/2004 | Radke et al. | 73/24.06 |
| 2003/0117619 | A1 | * | 6/2003 | Vo-Dinh et al. | 356/318 |
| 2004/0128977 | A1 | * | 7/2004 | Wilson et al. | 60/204 |
| 2004/0216785 | A1 | * | 11/2004 | Bowe et al. | 137/599.12 |

* cited by examiner

*Primary Examiner* — Stephen M Hepperle
*Assistant Examiner* — Atif Chaudry
(74) *Attorney, Agent, or Firm* — Ulysses John Biffoni

(57) ABSTRACT

A flow modulator to control the flow of an aerosol to an aerosol detection and/or monitoring system and other aerosol flow systems includes a chamber having an inlet and an outlet, a diverging section of the chamber beneath the inlet that has a flow divider at the center to divide the aerosol into fractions, a recirculation section in which the divided aerosol fractions are recombined, and a converging section that channels the recombined aerosol fractions to the outlet of the chamber.

10 Claims, 3 Drawing Sheets

US 7,997,300 B1

AEROSOL INLET FLOW MODULATOR

GOVERNMENT INTEREST

The invention described herein may be manufactured, licensed, and used by or for the U.S. Government.

TECHNICAL FIELD

The present invention relates in general to aerosol detection and identification systems, and more particularly to monitoring systems that collect and analyze aerosol samples from the surrounding environment.

BACKGROUND

An aerosol, as used herein, is a relatively stable suspension of fine solid or liquid particles in a gas, especially air. The atmosphere contains a vast array of trace particulates. These particles may be biological, chemical, or radiological in origin, and may result from terrestrial processes such as weather, fires, volcanoes and earth quakes, animal and human activities, and other sources. At any given time, an air sample may contain minerals, dust, pollen, mold, live and dead microorganisms and their products, trace chemical vapors, and so forth, and the mix is constantly changing.

An increasing number of systems are used to detect and analyze aerosols, ranging from systems that measure and monitor the amount of pollen, dust, mold and pollutants in the air, to systems that detect minute amounts of highly toxic biological, chemical and radiological warfare agents. Such systems may be designed for open-air environment point detection applications and/or indoor point detection applications. Both high level and low level monitoring systems are in use. For example, high level monitoring systems may be used in industrial applications where very high concentrations of aerosols are found, such as in sawmills, foundries, livestock facilities, and the like. Lower level monitoring systems are needed in industrial and healthcare applications such as semiconductor fabrication "clean rooms," and hospital operating rooms. Still other highly sensitive systems are designed for detection and monitoring of airborne chemical and biological warfare agents.

An aerosol collector is generally used by detection and monitoring systems to extract and concentrate aerosol samples from the surrounding environment which are then analyzed for target aerosols. While a number of different sampling methods are employed depending on the application, aerosol collectors typically rely on a consumable collection media that requires servicing from time to time. Thus, the collectors are configured to operate only when there is a reason to suspect that there may be aerosol particles of interest in the surrounding air. The task of deciding when to activate the collector is performed by a "trigger" or "cue" component. In certain sophisticated aerosol detection systems, for example, the trigger component continually samples the air and interrogates aerosol particles for fluorescence signatures that characterize particles of interest. When it detects a characteristic aerosol particle in sufficient concentration it "triggers" the collector to collect a sample for detailed analysis. Unfortunately, the presence of certain particulates in sufficient numbers may retard or inhibit the trigger's ability to accurately detect the presence or absence of particulates of interest resulting in false triggering or other malfunctions. For example, diesel exhaust, road dust, burning vegetation, ethylene glycol vapor and fog oil are all known to cause triggering errors in aerosol detection systems. Such triggering errors can result in premature system failure, false positive and false negative detection errors and increased servicing costs.

A variety of hardware and software active and passive filter elements have been devised to compensate for the presence of interferents in order to reduce false triggering events. Although such filtering elements add to the cost and complexity of a detection system, the results have been less than satisfactory and interferent rejection continues to be a significant problem for aerosol detection systems.

Embodiments according to the present invention employ a different approach from such filtering and compensation systems and substantially reduce the likelihood of triggering errors by providing an elegant and highly effective flow modulator at the input to a triggering/cueing component of an aerosol detection system.

SUMMARY

In general, in one aspect, an embodiment of a flow modulator for an aerosol sampler according to the present invention includes a chamber having an upstream end and a downstream end that has an inlet proximate the upstream end and an outlet proximate the downstream end. The chamber includes a first section beneath the inlet that progressively expands in size as it extends toward the downstream end, a second beneath the first section that extends toward the downstream end and a third section positioned beneath the second section that progressively contracts in size as it extends toward the downstream end. The flow modulator also includes a flow divider disposed within the chamber and positioned substantially at the center of the first section. The flow divider is dimensioned to cause airflow through the chamber to follow multiple pathways including a main airflow pathway which traverses the periphery of the flow divider and a core airflow pathway which traverses a passage substantially at the center of the flow divider.

In general, in another aspect, a method for modulating an aerosol flow containing aerosol pulses or boluses according to the present invention includes providing a chamber that has an inlet at an upstream end, an outlet at a downstream end and an expansion cavity, providing a flow divider to cause the aerosol flow to traverse a plurality of pathways into the expansion cavity, channeling the aerosol flow to the inlet, dividing the aerosol flow into fractions in the chamber, recirculating the fractions in the expansion cavity to effect a plurality of dwell times for the fractions and recombining the fractions with fractions from preceding boluses or pulses before the aerosol flow exits from the chamber outlet. In still other aspects, the method for modulating an aerosol flow containing aerosol pulses or boluses according to the present invention includes providing a chamber that has a diverging section in which the cross sectional area increases toward the downstream end and a converging section positioned beneath the diverging section in which the cross sectional area decreases toward the downstream end and providing a flow divider that is positioned inside the chamber.

DETAILED DESCRIPTION

In the following detailed description, reference is made to the accompanying drawings. The drawings illustrate specific embodiments in which the invention, as claimed, may be practiced. The invention, however, may be embodied in many different forms and should not be construed as limited to the embodiments set forth. Rather, these embodiments are provided so that this disclosure will be thorough and complete, and will fully convey the scope of the invention to those skilled in the art. As will be appreciated by those of skill in the art, the present invention may be embodied in methods, systems and devices. Wherever possible, the same reference numbers will be used throughout the drawings to refer to the same or like parts.

Figure 1:
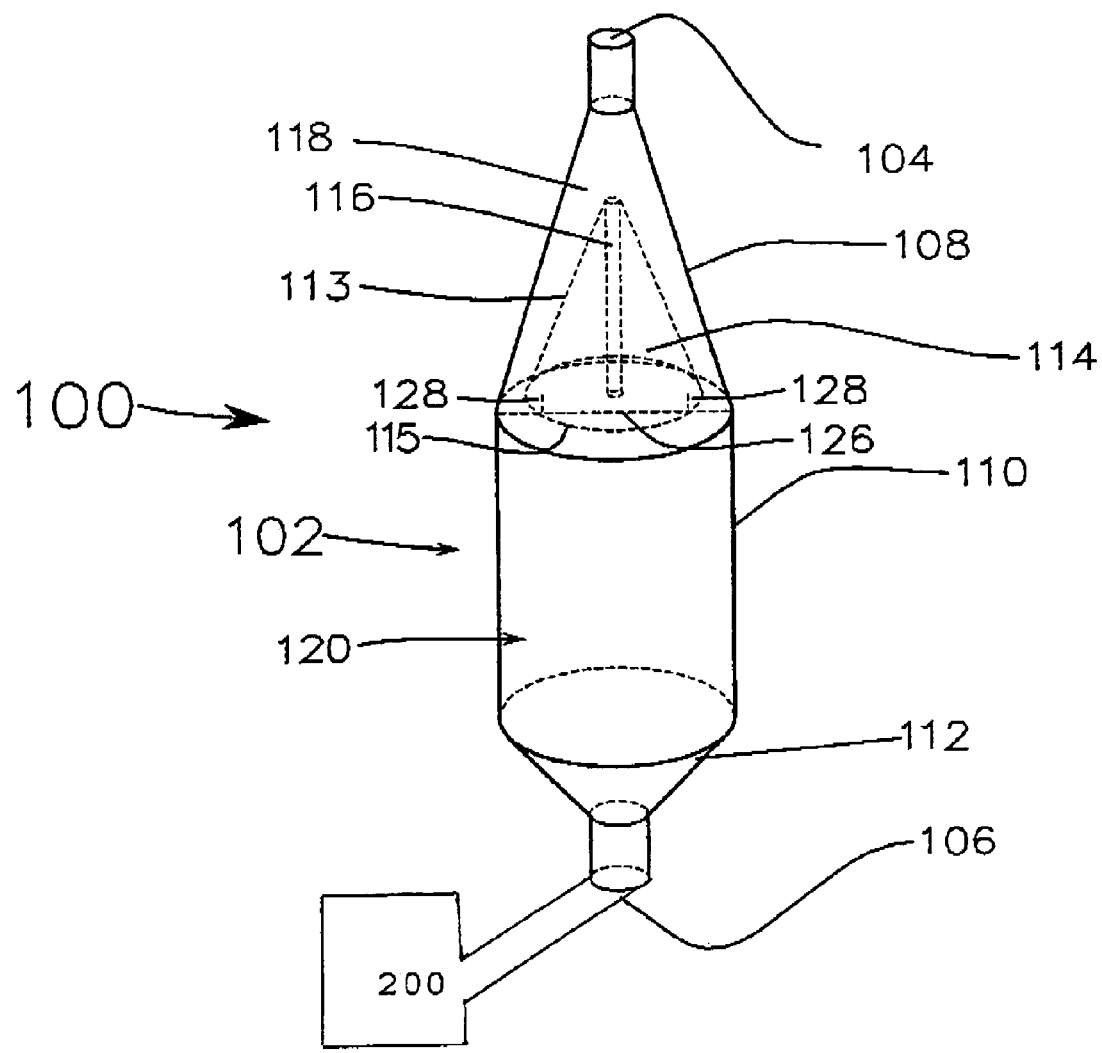
FIG. 1 shows a front perspective view of an embodiment of a flow modulator according to the present invention.

FIG. 1 shows a flow modulator 100 according to a first and preferred embodiment of the present invention. Flow modulator 100 includes a multi-sectioned, air-tight expansion chamber 102 that has an inlet tube 104 at an upstream end, shown at the top of FIG. 1, and an outlet tube 106 at a downstream end, shown at the bottom of FIG. 1. Inlet tube 104 and outlet tube 106 are fluid conduits dimensioned and configured with appropriate fittings to enable flow modulator 100 to be installed in-line between an intake aerosol sampling tube (not illustrated) and an aerosol intake port of a trigger component of an aerosol detection system 200. Flow modulator 100 is adapted to control and dampen a gaseous aerosol-containing flow, such as ambient air, provided to the intake port of a trigger component of an aerosol detection system 200 or to similar aerosol sampling apparatus.

Chamber 102 essentially provides an expansion cavity through which the intake aerosol flows before entering the sampling device. Chamber 102 may be constructed from a variety of materials including sheet metal, plastics or composites. Smooth inner surfaces and seamless construction are preferred to minimize air turbulence and particle deposition. Conductive materials are also preferred to prevent the buildup of electrostatic charge which may precipitate the aerosol particles.

Chamber 102 includes three basic regions from top to bottom: a diverging section 108 that increases in cross-sectional area as it extends toward the downstream end, a middle section 110 that is joined to diverging section 108 and maintains substantially the same cross sectional area for its entire length, and a converging section 112 that is joined to the base of middle section 110 and decreases in cross sectional area as it extends toward outlet 106.

Figure 2:
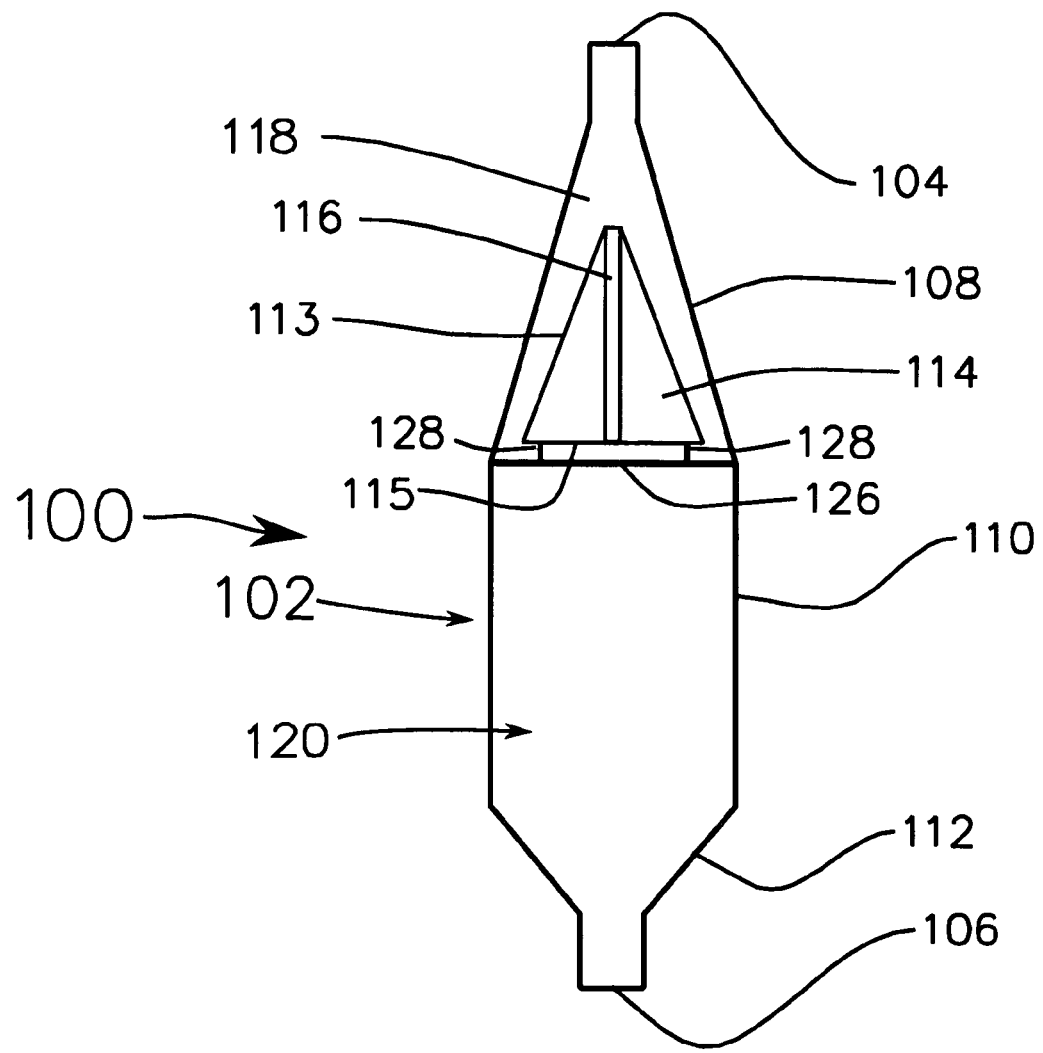
FIG. 2 shows a longitudinal sectional view of FIG. 1.

In the preferred embodiment, chamber 102 forms a circular cylinder overall, i.e., a cylinder having circular transverse cross sections centered on a longitudinal axis. A chamber 102 that is formed from a circular cylinder provides an even and balanced distribution of aerosol flow over the entire cross section and thus reduces the likelihood that dead zones or other regions of uneven airflow may cause particles to become trapped. More particularly, as shown in FIGS. 1-2, diverging section 108 forms an upright circular cone (i.e., a flared cylinder) that widens progressively from the radius of inlet tube 104 to a wider radius where it joins middle section 110. Middle section 110 extends downwardly for about the same length as diverging section 108 but maintains the same radius throughout (i.e., it forms a straight circular cylinder). Converging section 112 forms an inverted circular cone that tapers progressively from the radius of middle section 110 to the radius of outlet 106. Converging section 112 is generally shorter than either middle section 110 or diverging section 108. While a circular cylinder shape is preferred for chamber 102, in alternative embodiments, chamber 102, or any section thereof, may be generated from a surface of revolution or extruded from a shape that is not round, such as a cylinder that has an elliptical or parabolic cross section, or the like.

Flow modulator 100 also includes a flow divider 114 that is positioned within diverging section 108, substantially at the center and which causes the airflow to be diverted along a number of different paths. Flow divider 114 is substantially similar in shape to diverging section 108, but small enough to provide space for an outer radial passage 118 between the sidewall of diverging section 108 and the sidewall of flow divider 114 through which most of the airflow will pass. In this embodiment, flow divider 114 is cone-shaped and extends from an apex located near the top of diverging section 108 to a base located just above the bottom of diverging section 108. Flow divider 114 also includes a narrow axial passage 116 extending from the apex to the base thereof. Flow divider 114 is positioned on two small upright spacers 128 that are attached to a narrow transverse support rod 126 extending across chamber 102 at the bottom of diverging section 108. Flow divider 114 is preferably made from a smooth surfaced metal, composite, or plastic material which may be substantially solid or may be hollow or partially hollow so long as external surfaces are smoothly joined and well sealed. A recirculation zone 120 is defined just beneath the base of flow divider 114 in middle section 110 and extends down to converging section 112.

In general, flow modulation in embodiments according to the present invention involves dividing an inlet aerosol flow into flow fractions and then recombining those fractions at different times. An aerosol stream is channeled into an expansion chamber where it is divided into fractions that traverse a number of different pathways into a recirculation zone where the fractions dwell for different times depending on their pathways. Most of the airflow is diverted by a flow divider positioned at the center of the expansion chamber above the recirculation zone. A smaller, core airflow follows a direct pathway through a center hole in the flow divider into the recirculation zone. The main airflow follows peripheral and less direct pathways into the recirculation zone which take more time to traverse than the core airflow path, and provide a variety of path lengths, flow impedances and transit/dwell times for fractions. Fractions of different dwell times are recombined in the recirculation zone and thereafter exit the chamber. The more rapidly moving core airflow sweeps lingering fractions out of the recirculation zone and generally improves circulation through the device.

Figure 3:
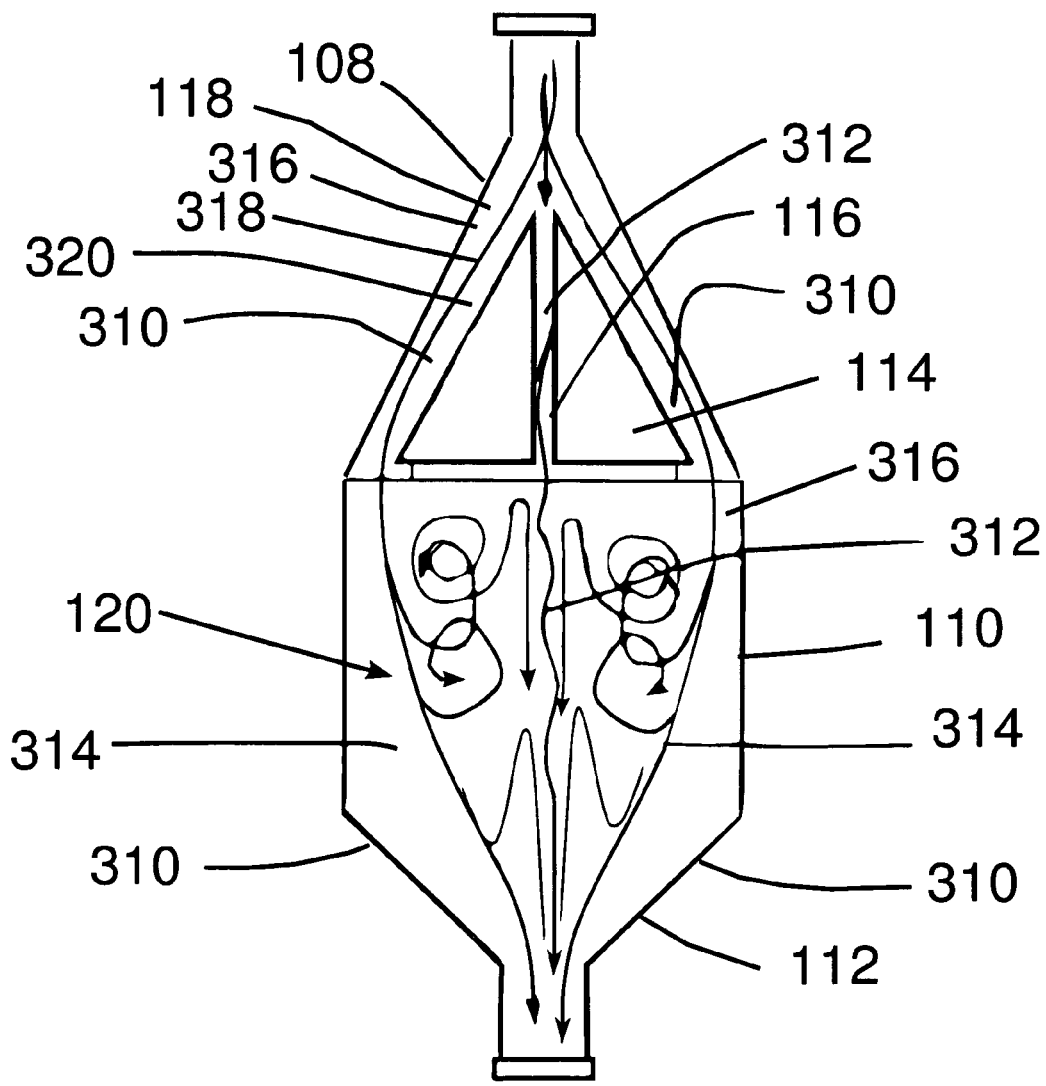
FIG. 3 shows a conceptual cutaway view of an embodiment of a flow modulator according to the present invention with airstreams representing generalized flow paths of aerosol through the device.

Referring to FIG. 3 as aerosol enters diverging section 108 a main inlet airflow 310 is distributed radially around flow divider 114 and travels through outer passage 1181 via a number of different pathways. A smaller core airflow 312 passes directly through flow divider axial passage 116. Core airflow 312 rejoins main airflow 310 in recirculation zone 120 after it exits axial passage 116 through the base of flow divider 114. Combining the core airflow 312 with the main airflow 310 in recirculation zone 120 reduces the likelihood that recirculating aerosol will dwell for an excessively long time.

In the preferred embodiment, in simplified terms, flow modulator 100 divides the main inlet airflow 310 into three basic streams: 1) An outer stream 316 that passes around flow divider 114 and along the inside wall of chamber 102 through diverging section 108, straight section 110, and converging section 112, and runs substantially straight to outlet 106; 2) A middle stream 318 that passes around flow divider 114 closer to the center of chamber 102 and into recirculation zone 120 where it circulates upstream toward the base of flow divider 114 and is then swept downstream by core airflow 312 through converging section 112 to outlet 106; and 3) A third inner stream 320 which passes very near flow divider 114 as it enters diverging section 108. Fractions following third inner stream 320 circulate upstream toward the base of flow divider 114 in one or more gently curving rotational recirculation patterns 314 and remain in recirculation zone 120 the longest before migrating to the path of core airflow 312 and being swept downstream through converging section 112 and to outlet 106. Particle deposition and loss is minimized by providing recirculation patterns 314 that have relatively large radii of curvature and by keeping recirculation velocity relatively low. In addition, small-scale turbulence along recirculation path lines is kept relatively low.

The flow patterns described above have been idealized for purposes of illustration into three models. Actual flow patterns transition more gradually and follow many more pathways. As can be seen from the streamlines of FIG. 3, however, the paths illustrated vary in length and complexity and provide correspondingly different dwell times for each fraction.

A variety of experimental and computational techniques may be used to arrive at dimensions for flow modulators according to the present invention. These dimensions will vary depending on input variables such as particle size, density, velocity, and other parameters of the aerosol as well as target recirculation dwell times. Other constraints such as size restrictions, cost, and availability of materials will also impact particular designs. Thus, the techniques discussed below are meant to be illustrative; other methods may be employed as would be understood by those of skill in the art.

In one example, a prototype embodiment of a flow modulator according to the present invention measures approximately 24 inches from top to bottom and has inlet and outlet tubes 104 and 106, respectively, of about 1.875 inches in length. Both the diverging section 108 and middle section 110 are 8.75 inches in length and 6 inches in diameter on the inside (widest diameter of diverging section). Flow divider 114 is a solid cone measuring 4.5 inches in diameter at the base and 6 inches in height with axial passage 116 is ⅜ inch in diameter. Converging section is 2.75 inches in height.

A combination of experimental and computational two-dimensional (2-D) models using smoke, water-dye, and Particle Image Velocimetry (PIV) flow visualization were used to refine the shape and size of the prototype flow modulator components to arrive at a target recirculation dwell time (2 seconds was estimated to be the most useful). Computational Fluid Dynamics (CFD) flow modeling of the concept (in both 2 and 3 dimensional models) was also performed to optimize the flow divider position in the diverging section. The models identified flow patterns that could adversely affect aerosol transmission. Deposition visualization and aerosol transmission efficiency experiments were performed on the prototype flow modulator, which was fabricated from sheet metal, to characterize the actual performance of the design. Those experiments verified the existence of deposition sites indicated by the models, however, the data from the transmission efficiency tests showed that the actual amount lost to these deposition sites was negligible. An aerosol chamber test where the concentration of aerosol sampled through the flow modulator was compared to the chamber challenge concentration, showed the transmission of 5-micron particles to be essentially 100 percent.

To evaluate the effectiveness of the prototype flow modulator in connection with a Biological Agent Warning System (BAWS) type trigger system, two BAWS units were placed side-by-side in a breeze tunnel facility. One of the systems was equipped with the prototype flow modulator and the other was not. Both inlet intakes were place in the recirculation zone of a bluff body and a diesel interferent was introduced to the 5 mph wind tunnel air stream. Puffs of an aerosol simulant (3-micron polystyrene latex spheres) were introduced to the air stream in the presence of the diesel soot. The results of this test indicate that the flow modulator improved BAWS performance by: a) reducing the dynamic threshold of the system by removing rapid fluctuations of aerosol, b) improving the ability to detect threat simulants in the presence of exhaust, or reduced the "blinding" effect of exhaust, and c) reducing false trigger rates by shifting the spectral signature of the diesel out of the bio-threat region and by reducing the number of events exceeding the threshold for triggering.

CONCLUSION

In summary, embodiments according to the present invention provide a flow modulator that is capable of modulating and dampening fluctuations of aerosol flow inputs to detection systems without incurring significant aerosol particle transmission loss. This effect can greatly improve the performance of trigger systems in the presence of a blinding aerosol such as diesel exhaust. In particular, embodiments according to the present invention may be installed in-line between an inlet and a Biological Agent Warning Sensor (BAWS) unit which is used as a trigger detector for the Joint Biological Point Detection System (JBPDS) system. Other embodiments will find use in clean room, hospital and industrial biological and chemical detection and monitoring systems and in systems for monitoring and detecting biological and chemical aerosols in the open atmosphere. Embodiments of flow modulators according to the present invention substantially reduce the occurrence of rapidly changing concentrations of particulates that may "blind" a sampling system or otherwise contribute to false triggers by dampening inlet aerosol concentration fluctuations and spikes. In one aspect, incoming aerosol pulses or boluses are divided into multiple fractions, recirculated in an expansion cavity to effect different dwell times for fractions and are recombined with fractions from preceding or succeeding boluses or pulses before exiting the cavity and continuing through the inlet train of an aerosol detection system.

Systems according to the present invention are entirely passive in operation and do not require valves or actuators. In addition, systems according to the present invention do not rely on software or hardware filtering or compensation. A number of embodiments of the invention defined by the following claims have been described. Nevertheless, it will be understood that various modifications to the described embodiments may be made without departing from the spirit and scope of the claimed invention. For example, alternative embodiments may provide multiple parallel or series expansion chambers. Various other alternative embodiments may employ one or more inline flow dividers or diverters that are external to the expansion chamber. Accordingly, other embodiments are within the scope of the invention, which is limited only by the following claims.

What is claimed is:

1. A flow modulator in combination with a biological aerosol detection system, comprising:

a biological aerosol detection system having a trigger component with an inlet;

a chamber having a upstream end and a downstream end;

an inlet to the chamber proximate the upstream end;

an outlet from the chamber proximate the downstream end;

a diverging section of the chamber positioned downstream of the inlet that is substantially conical in shape and progressively expands in size as it extends toward the downstream end;

a middle section of the chamber positioned downstream of the diverging section that is substantially cylindrical in shape and extends toward the downstream end;

a converging section of the chamber positioned downstream of the middle section that is substantially conical in shape and progressively contracts in size as it extends toward the downstream end; and a flow divider disposed within the diverging section of the chamber, wherein said flow divider is substantially conical in shape having an apex and a base and progressively expands in size as it extends towards the downstream end, wherein said flow divider is rigidly affixed within the diverging section of the chamber, and wherein said flow divider has an axial passage located substantially at the center of the flow divider and extending from the apex to the base of the flow divider, so that the flow divider causes airflow through the chamber to follow multiple pathways, the pathways comprising a main airflow pathway which traverses an area between the flow divider and the diverging section of the chamber, and a core airflow pathway which traverses through the axial passage substantially at the center of the flow divider; and wherein said outlet is connected to said inlet of said trigger component of said aerosol detection system so that the entire modulated airflow is provided to the inlet of the trigger component to reduce false triggering of the aerosol detection system.

2. The flow modulator of claim 1, wherein said diverging section comprises a fractionating section which divides incoming airflow into fractions that traverse a number of pathways.

3. The flow modulator of claim 2, wherein said middle section comprises a recirculation section wherein the airflow fractions from the diverging section dwell for different times within the middle section before flowing into the converging section and exiting the flow modulator.

4. The flow modulator of claim 1, wherein the flow divider is positioned within the diverging section on two upright spacers attached to a transverse support rod extending across the chamber at the downstream end of the diverging section.

5. The flow modulator of claim 1, wherein said chamber is constructed of metal, plastic, or composites.

6. The flow modulator of claim 1, wherein the converging section is shorter in length than either the diverging section or the middle section.

7. The flow modulator of claim 1, wherein the diverging section and the middle section are of about the same length.

8. The flow modulator of claim 1, wherein the flow divider is constructed of metal, plastic, or composite having a smooth surface.

9. The flow modulator of claim 1, wherein the chamber and flow divider are constructed of conductive materials.

10. The flow modulator of claim 1, wherein the core airflow pathway created by the axial passage through the flow divider serves to sweep recirculating airflow out of the middle section of the chamber through the converging section of the chamber to the outlet.

* * * * *